United States Patent [19]

Hosoi et al.

[11] Patent Number: 4,541,952
[45] Date of Patent: Sep. 17, 1985

[54] PURIFICATION METHOD OF HUMAN INTERFERON

[75] Inventors: Kazuo Hosoi, Kamakura; Hitoshi Ozawa, Hiratsuka, both of Japan

[73] Assignee: Toray Industries, Inc., Tokyo, Japan

[21] Appl. No.: 494,021

[22] Filed: May 12, 1983

[30] Foreign Application Priority Data

May 17, 1982 [JP] Japan ................................. 57-81505

[51] Int. Cl.$^4$ ............................................. A61K 45/02
[52] U.S. Cl. ................................. 260/112 R; 424/85; 435/68; 435/811
[58] Field of Search ...................... 260/112 R; 424/85; 435/68, 272, 811

[56] References Cited

U.S. PATENT DOCUMENTS

| | | | |
|---|---|---|---|
| 4,257,938 | 3/1981 | Hosoi | 260/112 R |
| 4,278,661 | 4/1981 | Knight | 260/112 R |
| 4,289,689 | 9/1981 | Friesen | 260/112 R |
| 4,359,389 | 11/1982 | Heine | 210/644 |

FOREIGN PATENT DOCUMENTS

| | | |
|---|---|---|
| 8002229 | 10/1980 | European Pat. Off. .............. 424/85 |
| 0011435 | 11/1979 | Fed. Rep. of Germany . |
| 0027262 | 10/1980 | Fed. Rep. of Germany . |

OTHER PUBLICATIONS

Colowick and Kaplan, Eds.: *Methods in Enzymology*, "Interferons", Part A, vol. 78, Pestka, Ed. Academic Press, 1981.
W. J. Jankowski et al., Biochemistry, 15, 5182–5187 (1976).
E. Bollin et al., Preparative Biochemistry, 8, 259–274 (1978).
J. S. Erickson et al., Archives of Virology, 63, 253–261 (1980).
E. Knight, Jr., et al., Science, 207, 525–526 (1980).
H. Friesen et al., Archives of Biochemistry and Biophysics, 206, 432–450 (1981).
V. G. Edy et al., J. Biol. Chem., 252, 5934–5935 (1977).
K. C. Chada et al., J. Gen. Virol., 43, 701–706 (1979).
J. W. Heine et al., J. Gen. Virol., 54, 47–56 (1981).
Berg et al., The Complete Purification of Human Leucocyte Interferon, Scand. J. Immunol., 11, pp. 489–502, 1980.

*Primary Examiner*—John Kight
*Assistant Examiner*—Garnette D. Draper
*Attorney, Agent, or Firm*—Cushman, Darby & Cushman

[57] ABSTRACT

A method for the purification of human interferon by the successive treatments of a crude interferon solution with an immobilized carrier which is coupled with a blue dye and a chelating carrier which contains a chelating residue chelated with at least one metal ion selected from the group consisting of $Co^{2+}$, $Ni^{2+}$ and $Zn^{2+}$.

22 Claims, No Drawings

PURIFICATION METHOD OF HUMAN INTERFERON

This invention relates to a method for the purification of human interferon, especially human β-interferon.

Interferon is a protein having antiviral activity which is produced by living cells when they are stimulated by viruses or by other specific reagents.

When an animal tissue or cell is treated with interferon, the tissue or cell becomes resistant to infection by various viruses (antiviral state). Infection by wide range of viruses can be prevented by the antiviral state and, in this sense, interferon is virus-nonspecific. On the other hand, interferon has species or origin specificity. The cells of certain species can attain an antiviral state only when the cells are treated with an interferon originated from the same species. The action of interferon is not restricted to antiviral activity. It has been also reported that it has potential antitumour activity, inhibitory activity toward cell growth, activation of macrophage activity and the like.

Owing to these activities, interferon is expected to be a promising medicament not only for the treatment and prophylaxis of viral diseases such as viral hepatitis B, herpes, influenza, etc. but also the treatment of cancerous conditions such as encephaloma, osteosarcoma, leukemia, etc.

However, the interferon used for therapeutic purposes should be human interferon which is produced by human cells due to its specificity of the species.

There are three kinds of human interferons. The first is α-interferon which is produced by human lymphocyte cells or by other lined cells. The second is β-interferon which is produced by human fibroblast cells or by other lined cells. The third is γ-interferon which is produced by human T-lymphocytes.

The human interferons (hereinafter referred to as an interferon), for example β-interferon are generally produced by the following method:

β-interferon can be produced from fibroblast cells or established cell lines which are cultured on a glass surface, a suitable plastic surface, or on microcarrier such as DEAE-dextran. The cells are treated with double strandard RNA such as Poly I: Poly C (induction step) and then with cycloheximide and actinomycin D (super induction step), by which induction procedures the cells begin the production of β-interferon for the following 20–48 hours. The Eagle MEM medium (if necessary, enriched with serum) is usually used for the production of β-interferon, but other nutrients or additives may be added.

The crude interferon solution thus obtained contains a very small amount of interferon ($10^3 - 10^5$ IU/ml = $10^{-6} - 10^{-4}$ mg/ml) and many impurities originating grom the cells and the culture medium. Consequently, the concentration and purification of the crude interferon is a prerequisite to its use for therapeutic purposes. Pure interferon is believed to have a specific activity of about $0.4 - 1 \times 10^9$ IU/mg protein.

As the conventional methods for the concentration and purification of crude interferon, precipitation method (for example, by using ammonium sulfate), ultrafiltration (for example, by using hollow fibrous membrane), ion exchange chromatography (for example, by using CM-Sephadex ® [Pharmacia Fine Chemicals, hereinafter referred to as Pharmacia]), gel chromatography (for example, by using Sephadex ® [Pharmacia]), etc. were employed. However, these methods are not practicable since a very small amount of interferon can be recovered.

Numerous methods have been recently reported as being successful for the purification of interferon.

The hydrophobic chromatography by using concanavalin A-, octyl-, tryptophyl-, or phenyl-agarose was reported by Carter et al [Biochemistry, 15, 704(1978); J. Biol. Chem. 251, 5381 (1976); ibid., 251, 7260 (1976)].

It was reported by Jankowski et al [Biochemistry, 15, 5182-5187(1976)] that interferon was bound to a carrier on which a blue dye which has the following formula and is called as CI Reactive Blue 2 was coupled.

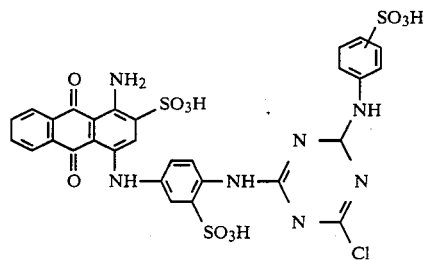

For such a purpose, Cibacron Blue F3GA ® or Cibacron Blue 3GA ® (CIBA-GEIGY Co.) was used. Similar purifications to the Jankowski's method were reported by Bollin et al [Preparative Biochemistry, 8, 259-292(1978)] and by Erickson et al [Archives of Virology, 63, 253-261(1980)]. In the case of this immobilized blue chromatography, it was reported by Knight et al [U.S. Pat. No. 4,278,661] that the recovery, purity and specific activity of the purified preparation is satisfactory (50%, more than 95% and $4 \times 10^8$ IU/mg protein, respectively).

However, the removal of the impurities including the pyrogenic substances is unsatisfactory. Consequently, the desalination step before its use is necessary to remove ethyleneglycol and sodium chloride in the interferon preparation according to the known procedures such as gel-chromatography using Sephadex G 25 ®, dialysis, etc. However, ethyleneglycol was difficultly removed due to its high viscosity. Further, the immobilized blue carrier has higher affinity toward actinomycin D as a super inducer for the production of interferon, so that actinomycin D which also acts as a strong mutagen is apt to contaminate the recovered interferon fraction. These result in a critical defect for its use as an injectable.

Zinc chelate chromatography was reported by Edy et al [J. Biol. Chem., 252, 5934(1978)]. In this method, about 14 times the column volume of the original interferon solution was charged to a column containing a zinc chelate carrier. After elution with an acidic solution, the interferon was obtained which was purified 32 times. When elution was performed using the pH gradient elution method, 3100 times purification was achieved and there was obtained a purified preparation having a specific activity of $10^{8.5}$ IU/mg protein. This chromatographic system seems good but still has shortcomings of incapable of dealing with a large quantity of interferon solution, so that this system is appeared to be impractical. Judging from the results, the elution profile of interferon is lacking in sharpness and a rather large volume of eluant is needed. Consequently, the interferon titer of recovered solution is not very high (about $1.1-2 \times 10^5$ IU/ml).

A combination of concanavalin A-agarose chromatography with zinc chelate chromatography for the purification of interferon was reported by Sulkowski et al [J. Gen. Virol., 43, 701–706(1979)]. In this method, the interferon recovered from the above-mentioned agarose column with 50% ethyleneglycol was subjected to the zinc chelate chromatography. As the result, 100% of the charged interferon activity was found in the passed-through fractions. For overcoming this problem, the dialysis of the interferon recovered from the agarose column against 1M sodium chloride solution containing 20 mM sodium phosphate is needed.

A combination of porous glass beads with zinc chelate chromatography was reported by Heine et al [Japanese Patent Laying Open No. 73028/71]. In this method, the dialysis step of the interferon fraction recovered from the porous glass beads was necessary before subjecting to the zinc chelate chromatography since the elution from the porous glass beads is performed at a pH 2.

As above, any of the prior methods cannot provide the highly purified and highly concentrated interferon preparation with appreciable recovery when dealing with a large quantity of crude interferon.

An object of this invention is to provide a purification method for interferon which overcomes the aforementioned disadvantages of the prior methods.

Another object of this invention is to provide an economic purification method for interferon which can be applicable for use with a large quantity of crude interferon solution and to provide a highly purified and highly concentrated interferon preparation with appreciable recovery.

According to this invention, a crude interferon solution produced by human cells is treated with an immobilized blue carrier. The interferon adsorbed on the immobilized blue carrier is eluted with an eluant. The recovered interferon solution is then treated with a metal chelate carrier having a chelating residue and including at least one metal ion selected from the group consisting of $Co^{2+}$, $Ni^{2+}$ and $Zn^{2+}$. The interferon adsorbed on the metal chelate carrier is detached from the carrier to give a highly purified and highly concentrated interferon preparation.

The purification method of this invention can be used to purify any of the interferons including $\alpha$-, $\beta$- and $\gamma$-interferons, but it is preferred to employ $\beta$-interferon.

The crude interferon solution which is used in this invention is produced by human cells or established cell lines according to the known cell-culture method. And the interferon produced from the microorganisms such as E. coli, yeast, etc. to which interferon-producing genes have been integrated can be also used in this invention.

The crude interferon solution is firstly contacted with the immobilized blue carrier.

The blue dye, for example, the above-mentioned CI Reactive Blue 2, in this invention can be immobilized on any of a variety of commonly used carrier which are capable of coupling the dye. Such carriers include (A) coupling of the dye via the amino group of the anthraquinone moiety to cyanogen bromide activated agarose; (B) coupling of the dye to the cross-linked agarose gel by the triazine coupling method via an ether linkage; (C) coupling of Blue Dextran ® (dextran coupled with the blue dye; Pharmacia) to cyanogen bromide activated agarose by the triazine coupling method; (D) coupling of the blue dye which is bound to the side chain of Affi-Gel 10 ® (Bio-Rad Lab., hereinafter referred to as Bio-Rad) via peptide linkage to the polysaccharide carrier. Other carriers for example, a cross-linked dextran gel such as Sephadex ® (Pharmacia) and a vinyl polymer having hydroxyl groups can also be used. As the vinyl polymer having hydroxyl groups, which is also available as a carrier for metal chelate chromatography in the following step, a hydrophilic globular polymer such as Toyopearl ® (Toyo Soda Co.) is preferred.

It is preferred to employ the blue agarose gel corresponding to (B) because it has highly effective binding action to interferon, it does not cause the detachment of dye from the carrier since the coupling of the dye to the carrier is very stable under the pH condition of 6 to 13, and it can be easily commercially available. Such a blue agarose gel has the following structure and is commercialized under the trade name of "Blue Sepharose CL-6B (Pharmacia)", "Matrix Gel Blue A ® (Amicon Corp.)" and "Affi-Gel Blue ® (Bio-Rad)".

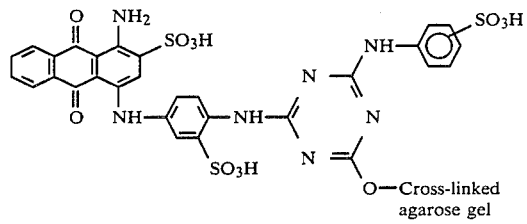

For the contacting of the immobilized blue carrier with the crude interferon solution, either a batch-wise method or a column-wise method can be used.

The immobilized blue carrier is usually contacted with interferon at a pH of 5 to 9 although the contact can be carried out at a pH of about 7 to 7.5 with which the crude interferon solution is produced. When some insoluble materials are observed in the original interferon solution, it is preferable to remove the insoluble materials in advance either by centrifugation or filtration. Further, it may be possible to raise the ionic strength of the solution in advance by adding a neutral salt such as sodium chloride, etc.

The contact of the crude interferon solution with the immobilized blue carrier is continued until practically all of the interferon activity is adsorbed on the immobilized blue carrier. In the case of column-wise method, a space velocity of $1-20$ $hr^{-1}$ is preferred. In the case of batch-wise method, the contact is continued for 1–100 hours. A sufficient amount of the immobilized blue carrier should be used which would adsorb most of the interferon activity. The adequate volume of the immobilized blue carrier is usually 1/10–1/10000 times the volume of the crude interferon solution. After the completion of adsorption, the immobilized blue carrier is washed with sufficient water, phosphate buffer solution, 6% sodium chloride solution, saline solution with or without not more than 30% of ethyleneglycol or propyleneglycol, etc. A portion of any proteinaceous impurities and pyrogenic substances present is removed during this washing step.

For the elution of partially purified interferon, suitable solutions buffered at a pH of 6–8 may be used. As such solutions, aqueous sodium chloride solution (0.5–2M) containing 45–70% by volume of ethyleneglycol or 40–55% by volume of propyleneglycol is recommended. A sufficient amount of eluant should be used which would recover substantially all of the interferon adsorbed on the immobilized blue carrier.

The eluate from the immobilized blue carrier is then subjected to a metal chelate chromatography. The carriers for the metal chelate chromatography which are used in this invention are polysaccharides, cross-linked polyolefine derivatives or vinyl polymer having hydroxy groups, which have chelating groups such as biscarboxymethyl imino group and a transition metal ion bound to the chelating group. As the vinyl polymer having hydroxy groups which is also available as the carrier for the blue dye chromatography, the hydrophilic polymers in a globular form is preferred. Among them, insoluble polysaccharide derivatives having a chelating group such as a biscarboxymethyl imino group and a transition metal ion chelated thereto is used. For example, the following carrier which was reported by Porath et al [Nature, 258, 598 (1975)] is applicable for this purpose:

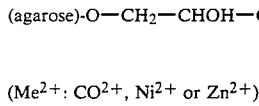 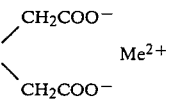

$(Me^{2+}: Co^{2+}, Ni^{2+} \text{ or } Zn^{2+})$

The carrier for the metal chelate chromatography is prepared according to the method of Porath.

Sodium iminodiacetate (14 g) and sodium carbonate (20 g) is dissolved in water (100 ml) and reacted with Epoxy-activated Sepharose 6B ® (135 ml, wet volume) for 16 hours at 56° C. (The chelating capacity of the carrier is about 15–30 μmoles/ml of the wet carrier when Epoxy-activated Sepharose 6B ® (Pharmacia) is used, but other carriers which have different chelating capacities are also acceptable.) After filtration and washing, the carrier is treated with 1M ethanolamine solution (100 ml) for 4 hours at 56° C., filtered and washed. After loading a suitable amount of the thus-obtained carrier into a column, sterilizing and washing, an acetic acid-sodium acetate buffer solution (pH 4.7) is passed through the column to keep at pH 4.7. 1% of transition metal salt solution is passed through and washed with water or weakly acidic solution to obtain a metal chelate carrier having a capacity of about 30 μmoles/ml. Before use, washing of the carrier with a buffer solution is recommended.

The transition metal ions which are used in this invention comprise at least one metal ion selected from the group consisting of $Co^{2+}$, $Ni^{2+}$ and $Zn^{2+}$.

The metal chelate carrier makes contact with the interferon solution recovered from the immobilized blue carrier at a pH between 5.6–9. Preferably, a pH of 7–8 is utilized. When the concentration of ethyleneglycol or propyleneglycol in the recovered solution from the immobilized blue carrier is high, adjustment of the concentration by diluting it with water is recommended. Both batch-wise and column-wise methods are of course applicable for this contact step, but the latter is preferred. The amount of the metal chelate carrier and the contact time should be selected so as to adsorb essentially all of the interferon activity on the metal chelate carrier. After adsorption of the interferon, washing the metal chelate carrier with either water, saline solution or an appropriate buffer solution is recommended. During this washing procedure, a large portion of the contaminated protein and pyrogenic substances which still remain in the interferon fraction can be removed.

The elution of interferon from the metal chelate carrier is performed either with an acid solution or a solution of chelating reagents. As the acid solution, a solution of an organic acid, inorganic acid, salt of an organic acid, salt of inorganic acid, or a mixture thereof can be used. The pH of the acid solution is not more than about 6, preferably 3 to 5. For such a solution, an acetic acid-sodium acetate buffer solution (pH 4–5) or citric acid-sodium phosphate buffer solution (pH 4.5) with or without sodium chloride, etc. can be suitably used. The concentration of this eluant is preferably about 0.01–1M.

Another method of elution is through the use of a solution of a chelating reagent. Chelating reagent which may be used include EDTA, imino diacetic acid, histidine, etc. which are known to have chelating activity towards transition metal ions. Histidine is considered as one of the more preferable reagents to be used. In the use of histidine solution, both a solution of histidine hydrochloride and histidine itself can be used. Especially, 0.01–0.2M histidine solution containing sodium chloride is preferable.

The concentration or the pH of the eluant is changed continuously or stepwise so as to fractionally collect the eluate, thereby collecting a fraction containing higher purified interferon.

To the highly concentrated and highly purified interferon solution thus obtained as above, human serum albumin or human plasmanate protein for stabilization is added. The salt or metal ion is removed either by dialysis against water, a dilute salt solution or a dilute acid solution or by gel-chromatography, for example on Sephadex G-25. The desalinated interferon solution is, after pH adjustment (if necessary) and aseptic filtration, liophillized to yield an interferon preparation which is suitable for intramuscular or intravenous injection. Some additives, which are effective for the stabilization of interferon such as lactose, human albumin etc. may be added before aseptic filtration.

The immobilized blue carrier as well as the metal chelate carrier are repeatedly utilized by subjecting the following treatment. A suitable solution such as 0.1N sodium hydroxide, 0.5M sodium hydroxide plus 8M urea, etc. is passed through the immobilized blue column after recovering the partially purified interferon to remove the contaminated substances which still remain in the carrier without eluting. And then, the column is sterilized and washed with water or an aqueous sodium chloride solution. In a case of metal chelate carrier, a suitable solution such as histidine solution, EDTA solution, etc. is passed through the metal chelate column after recovering the purified interferon to remove the metal ions. Successively a suitable solution such as 0.1N sodium hydroxide, etc. is passed through the column to remove the contaminated substances which still remain in the carrier followed by sterilizing and washing the column with an aqueous sodium chloride solution or water. After then, the metal ion can be bound with the washed carrier according to the aforementioned procedure to form the metal chelate carrier.

The merit of the purification method of this invention is more clearly understood when the result of this method is compared with that of a method which provides for the separate use of the immobilized blue carrier or the metal chelate carrier, respectively.

When a 50 column volume of crude interferon solution is applied to metal chelate column, substantially all of the interferon activity is retained on the column and nearly quantitative elution could be achieved by the elution with 0.2M histidine solution containing 0.2M sodium chloride. However, when the charge volume was increased to 150 columns volume, most of the interferon activity was found in the passed-through fractions. The column retained small amount of the applied interferon activity. This fact is considered to be due to the presence of certain interfering substances which appeared to interfere with the adsorption of interferon onto the metal chelate carrier. The capacity of the metal chelate carrier towards the crude interferon solution is less than 150 times its volume and therefore, this method is unsuitable for any practical purpose.

In the case of the use of the immobilized blue carrier, the capacity of the immobilized blue carrier is sufficient for the crude interferon solution and the recovery of interferon activity from the column is satisfactory. The concentration of interferon in the eluate (about 100 times concentration) and the degree of purification (about 30 times purification) are also satisfactory. Consequently, the specific activity of interferon is high (about $1 \times 10^7$ IU/mg protein). However, the removal of the pyrogenic substances and actinomycin D is unsatisfactory so as to result in a critical defect for its use as an injectable.

The results of this invention show that when the partially purified interferon solution by the immobilized blue carrier treatment was applied to the metal chelate column, the capacity of the column increased markedly and one volume of the metal chelate carrier could adsorb almost completely interferon which was originally contained in about 3000 volumes of the crude interferon solution. Consequently, it was easy to obtain a highly concentrated and highly purified (specific activity: about $1-4 \times 10^8$ IU/mg protein) interferon solution with appreciably high recovery. In addition, significant portions of the contaminated heteroprotein such as bovine-albumin or globulin, actinomycin D and the pyrogenic substances which could not be removed by the immobilized blue carrier treatment were removed during the metal chelate chromatography, whereby a highly useful injectable interferon preparation was obtained.

The following Examples serve further to illustrate the invention, but are not intended to define or to limit the scope of the invention, which is defined in the appended claims.

EXAMPLE 1

A crude interferon solution used was prepared by treating human fibroblast cells in an Eagle-MEM medium containing 0.4% methylcellulose with Poly I: Poly C and then treating with cycloheximide and actinomycin D.

To 30 l of the crude interferon solution which had an interferon activity of $6.2 \times 10^6$ IU, 21 mg of protein and 100 μg of actinomycin D per l, 30 ml of blue agarose gel (Affi-Gel Blue ®, Bio-Rad) was added. After stirring for 40 hours and allowing to stand for 3 hours, the supernatant was removed and the agarose gel was transferred into the column while washing with a saline solution containing phosphate acid buffer. The supernatant was removed again. The column was washed twice and eluted. The washing solutions and the eluant used were as follows;

first washing solution (320 ml): 1.0M sodium chloride solution containing 10 mM sodium phosphate (pH 7.2)

second washing solution (280 ml): 25% ethyleneglycol solution containing 10 mM sodium phosphate and 1.0M sodium chloride (pH 7.2)

eluant (400 ml): 55% ethyleneglycol solution containing 10 mM sodium phosphate and 1.0M sodium chloride (pH 7.2)

The recovery of the partially purified interferon in the eluate (300 ml) from the original interferon solution was 81%, 33 times purification was achieved.

To the zinc chelate column (10 ml), the eluate (285 ml) from the blue agarose gel column was passed at a flow rate of 20 ml/hr. After washing twice, the column was eluted. The washing solutions and the eluant used were as follows;

first washing solution (300 ml): distilled water and 0.1M sodium phosphate solution (pH 6.7) being used at a flow rate of 30 ml/hr for 1 hour, alternately second washing solution (50 ml): 20 mM sodium citrate solution (ph 5.0)

eluant: 0.1M acetic acid-sodium acetate buffer solution (pH 4.5)

The recovery in the zinc chelate chromatography was 87% and the total recovery was 70%. 330 times purification was achieved.

The interferon activity, recovery, amount of protein and specific activity of each step are shon in Table 1.

TABLE 1

|  | Volume (ml) | Total interferon activity ($\times 10^6$ IU) | Recovery (%) | Total protein (mg) | Specific activity (IU/mg protein) |
| --- | --- | --- | --- | --- | --- |
| Starting material |  |  |  |  |  |
| crude interferon solution | 30,000 | 186 |  | 630 | $3.0 \times 10^5$ |
| Blue agarose gel column |  |  |  |  |  |
| supernatant | 32,000 | 3 |  | 570 |  |
| 1st washing solution | 320 | 0.2 |  | 20 |  |
| 2nd washing solution | 280 | 1.4 |  | 15 |  |
| elution fraction | 300 | 150 | 81 | 15 | $1.0 \times 10^7$ |
| Zinc chelate column |  |  |  |  |  |
| charging solution | 285 | 143 |  | 14 |  |

TABLE 1-continued

|  | Volume (ml) | Total interferon activity ($\times 10^6$ IU) | Recovery (%) | Total protein (mg) | Specific activity (IU/mg protein) |
| --- | --- | --- | --- | --- | --- |
| passed-through solution | 285 | 5 |  | 7 |  |
| 1st washing solution | 300 | 0.6 |  | 1.8 |  |
| 2nd washing solution | 50 | 10 |  | 4 | $2.5 \times 10^6$ |
| 1st elution fraction | 10 | 60 | 32 | 1.0 | $6 \times 10^7$ |
| 2nd elution fraction | 20 | 64 | 34 | 0.16 | $4 \times 10^8$ |
| total elution fraction | 30 | 124 | 70 | 1.2 | $1.0 \times 10^8$ |

Analysis of interferon activity by polyacrylamide gel electrophoresis

A part of the final eluate was dialyzed in the presence of sodium dodecylsulfate (SDS) and liophilized. After reducing the liophilized dialyzate with 2-mercaptoethanol, the reduced material was subjected to electrophoresis using polyacrylamide gel in the presence of SDS according to the method of Laemmli [Nature, 227, 680-685 (1970)] to analyze the interferon activity and dye with coomassie brilliant blue R 200. As the result, an interferon activity and a dark blue band were found only at a position of molecular weight of about 23,000.

Analysis of actinomycin D

Actinomycin D was analyzed according to the bioassay.

A part of the final eluate was desalined by the gel chromatography using Sephadex G 25 ® after adding human serum albumin (1 mg/ml). Additionally supplementing small amount of human serum albumin and lactose, the desalined eluate was filtered through a $0.2\mu$ filter and liophillized. Actinomycin D was found in an amount of not more than 0.0003 $\mu$g/$10^6$ IU interferon activity.

The eluate from the glue agarose gel column had 0.7 $\mu$g/ml of actinomycin D. The total amount of actinomycin D was 210 $\mu$g. In addition, the presence of actinomycin D in the eluate from blue agarose gel column was found from the absorption (430 nm) and bioassay.

A part of the eluate from blue agarose gel column was desalined by the gel chromatography using Sephadex G 25 ® after adding human serum albumin. Removing ethyleneglycol, the desalined eluate was liophilized. About 0.7 $\mu$g/$10^6$ IU interferon activity of actinomycin D was still found.

A rabbit pyrogen test

The liophilized material obtained as above from the final eluate was injected intravenously into three rabbits ($2 \times 10^5$ IU/kg body weight). The summation of pyrexia of these three rabbits was 0.5° C. In a case of injection at a dose of $2 \times 10^6$ IU/kg body weight, the summation of pyrexia was 0.6° C. The interferon purified according to this invention was negative to the rabbit pyrogen test.

The liophilized material obtained from the eluate of the blue agarose gel column was injected intravenously into three rabbits ($2 \times 10^5$ IU/kg body weight). The summation of pyrexia of three rabbits was 1.5° C. The interferon purification according to the blue agarose chromatography was doubtful negative to the rabbit pyrogen test.

EXAMPLE 2

A crude interferon solution similar to that used in Example 1 was used in this experiment.

20 l of the crude interferon solution was passed through a 20 ml of blue agarose (Matrex Gel Blue A ®; Amicon Corp.) column. The column was washed three times and eluted. The washing solutions and the eluant used were as follows;

first washing solution (200 ml): 1M sodium chloride containing 10 mM sodium phosphate (pH 7.2)

second washing solution (200 ml): 25% ethyleneglycol solution containing 10 mM sodium phosphate and 1M sodium chloride (pH 7.2)

third washing solution (40 ml): 40% ethyleneglycol solution containing 10 mM sodium phosphate and 1M sodium chloride (pH 7.2)

eluant (200 ml): 55% ethyleneglycol solution containing 10 mM sodium phosphate and 1M sodium chloride A zinc chelate column (5 ml) was connected to the outlet of the blue agarose column after the start of elution, and the eluate from the blue agarose column was directly passed through the zinc chelate column. Then the zinc chelate column was washed twice and eluted. The washing solutions and the eluant used were as follows;

first washing solution (200 ml): distilled water and 0.1M sodium phosphate (pH 6.7) being used alternately second washing solution (20 ml): 20 mM sodium citrate (pH 5.0)

eluant: 0.2M acetic acid-sodium acetate buffer solution containing 1M sodium chloride The interferon activity, recovery, amount of protein and specific activity of each step are shown in Tabel 2.

TABLE 2

|  | Volume (ml) | Total interferon activity ($\times 10^6$ IU) | Recovery (%) | Total protein (mg) | Specific activity (IU/mg protein) |
| --- | --- | --- | --- | --- | --- |
| Starting material |  |  |  |  |  |
| crude interferon solution | 20,000 | 142 |  | 1240 | $1.1 \times 10^5$ |
| Blue agarose column |  |  |  |  |  |
| passed-though solution | 20,000 | 10 | 7 | 1060 |  |
| 1st washing solution | 200 | 1 | 0.7 | 110 |  |
| 2nd washing solution | 200 | 1 | 0.7 | 1 |  |
| 3rd washing solution | 40 | 20 | 14 | 20 | $1.0 \times 10^6$ |
| Zinc chelate column |  |  |  |  |  |

TABLE 2-continued

| | Volume (ml) | Total interferon activity ($\times 10^6$ IU) | Recovery (%) | Total protein (mg) | Specific activity (IU/mg protein) |
|---|---|---|---|---|---|
| passed-though solution | 200 | 2 | 1.4 | 5 | |
| 1st washing solution | 200 | 1.3 | 0.9 | 2 | |
| 2nd washing solution | 20 | 27 | 19 | 1 | $2.7 \times 10^7$ |
| Total elution fraction | 20 | 82 | 58 | 0.4 | $2.1 \times 10^8$ |

EXAMPLE 3

20 l of crude interferon solution which had an interferon activity of $15 \times 10^6$/l and 60 mg/l of total protein was contacted with 40 ml of blue agarose carrier (Matrex Gel Blue A ®; Amicon Corp.). The carrier on which the interferon was adsorbed was charged on a column. Then, the column was washed twice and eluted. The washing solutions and the eluant used were as follows;

first washing solution (400 ml): 1M sodium chloride solution containing 10 mM sodium phosphate (pH 7.2)

second washing solution (400 ml): 25% ethyleneglycol solution containing 10 mM sodium phosphate and 1M sodium chloride (pH 7.2)

eluant (400 ml): 55% ethyleneglycol solution containing 10 mM sodium phosphate and 1M sodium chloride (pH 7.2)

100 ml of the interferon solution recovered from the blue agarose column was passed through 5 ml of a nickel chelate column. This nickel chelate column was washed and eluted. The washing solution and eluant used were as follows;

washing solution: distilled water and 0.1M sodium phosphate solution (pH 6.7) being used alternately eluant: 0.2M acetic acid-sodium acetate buffer solution containing 1M sodium chloride (pH 4.5)

The interferon activity, recorvery, amount of protein and specific activity of each step are shown in Table 3.

The final eluate contained very small amount of pyrogenic substances and was negative toward a Limulus test. Actinomycin D was not detected therein.

EXAMPLE 5

A strain of *E. coli* into which a structural gene of β-interferon had been integrated was cultured and the cultured strain was subjected to the procedures of bacteria-collecting, bacteria-grinding, removal of nucleic acid and precipitation with ammonium sulfate. A protein fraction containing β-interferon produced from the strain of *E. coli* was dissolved in a 25% ethyleneglycol solution containing 1M sodium chloride and 10 mM sodium phosphate(pH 7.2) to obtain a crude interferon solution. The crude interferon solution had $5 \times 10^6$ IU of interferon activity and 20 mg of protein per ml.

40 ml of the crude interferon solution was passed through 2 ml of the blue agarose (Matrex Gel Blue A ®; Amicon Corp.) column equilibratated with 10 mM sodium phosphate buffer solution containing 1M sodium chloride. The column was washed twice to remove about 95% of protein in the crude interferon solution and eluted while fractionating into each 2 ml fraction. The washing solutions and the eluant used were as follows;

first washing solution (10 ml): 25% ethyleneglycol solution containing 1M sodium chloride and 10 mM sodium phosphate second washing solution (10 ml): 40% ethyleneglycol solution containing 1M sodium chloride and 10 mM sodium phosphate eluant: 60% ethyleneglycol solution containing 1M sodium chloride and 10 mM sodium phosphate The eluate (12 ml) from the blue agarose column had $1.6 \times 10^7$ IU (80% recovery) of interferon activity and 6.4 mg of protein. The mean specific activity in each

TABLE 3

| | Volume (ml) | Total interferon activity ($\times 10^6$IU) | Recovery (%) | Total protein (mg) | Specific activity (IU/mg protein) |
|---|---|---|---|---|---|
| Starting material | | | | | |
| crude interferon solution | 20,000 | 300 | | 1,200 | |
| Blue agarose column | | | | | |
| 1st washing solution | | | | | |
| 2nd washing solution | | | | | |
| eluate | 400 | 260 | 87 | 26.0 | $1.0 \times 10^7$ |
| Nickel chelate column | | | | | |
| charging solution | 100 | 65 | | | |
| passed-through solution | | 0.7 | | | |
| 1st washing solution | | | | | |
| 2nd washing solution | | | | | |
| eluate | 20 | 55 | | 0.55 | $1 \times 10^8$ |

EXAMPLE 4

The procedure of Example 3 was followed except that a cobalt chelate column was used instead of a nickel chelate column.

The eluate (15 ml) had $4.5 \times 10^6$ IU of interferon (recovery 60%) and 0.25 mg of protein. The specific activity was $1.8 \times 10^8$ IU/mg protein. The final eluate was negative towards a Limulus test and actinomycin D was not detected therein.

fraction was $2.5 \times 10^7$ IU/mg protein (max: $5 \times 10^7$ IU/mg protein).

This eluate was analyzed in the similar manner to Example 1. As the result, the purity of the interferon activity at a position of molecular weight of about 19000 was 10–50% (mean 25%).

6 ml of the eluate recovered from the blue agarose column was passed through 1 ml of zinc chelate column equilibrated with 60% ethyleneglycol solution containing 1M sodium chloride and 10 mM sodium phosphate.

The column was washed three times and eluted. The washing solutions and the eluant used were as follows;
first washing solution (6 ml): 60% ethyleneglycol solution containing 1M sodium chloride and 10 mM sodium phosphate
second washing solution (6 ml): distilled water
third washing solution (6 ml): 20 mM sodium phosphate buffer solution containing 2M sodium chloride (pH 6.0)
eluant: 0.1M sodium acetate buffer solution containing 1M sodium chloride (pH 4.0) The final eluate (4 ml) had $4.0 \times 10^7$ IU (50% recovery) of interferon activity and 0.4 mg of protein. The specific activity was $1 \times 10^8$ IU/mg protein.

The final eluate was also analyzed in the similar manner to Example 1 to be found one band at a position of molecular weight of about 19000. The purity was more than 97%.

EXAMPLE 6

The procedure of Example 3 was followed except that 0.2M L-histidine-sodium chloride solution (pH 7.0) was used as an eluant of zinc chelate column.

The eluate (20 ml) had $50 \times 10^6$ IU of interferon (recovery 67%) and 0.5 mg of the total protein. The specific activity was $1.0 \times 10^8$ IU/mg protein.

What is claimed is:

1. A method of purifying human beta-interferon, comprising the successive steps of:
   (a) adsorbing a crude beta-human interferon solution on an immobilized blue carrier,
   (b) contacting the immobilized blue carrier with an eluant to produce an eluate containing the interferon,
   (c) contacting said eluate with a carrier having a chelating residue and including at least one metal ion selected from the group consisting of $Co^{2+}$, $Ni^{2+}$ and $Zn^{2+}$, wherein said metal ion is chelated to the chelating residue so a to absorb the interferon, and
   (d) contacting said carrier with an eluant to produce a purified and concentrated interferon solution.

2. The method according to claim 1, wherein said immobilized blue carrier is an immobilized carrier coupled with a dye.

3. The method according to claim 2, wherein said dye is CI reactive blue 2.

4. The method according to claim 2, wherein said immobilized carrier is cross-linked agarose gel.

5. The method according to claim 1, wherein said immobilized blue carrier is a carrier including a coupling of the CI reactive blue 2 to the cross-linked agarose gel via an ether linkage.

6. The method according to claim 1, wherein said carrier is a water-insoluble polysaccharide derivative having a chelating residue and including at least one metal ion selected from the group consisting of $Co^{2+}$, $Ni^{2+}$ and $Zn^{2+}$, wherein said metal ion is chelated to the chelating residue.

7. The method according to claim 1, wherein said carrier is a cross-linked polyolefine derivative having a chelating residue and including at least one metal ion selected from the group consisting of $Co^{2+}$, $Ni^{2+}$ and $Zn^{2+}$, wherein said metal ion is chelated to the chelating residue.

8. The method according to claim 1, wherein said carrier is a vinyl polymer containing a hydroxy group which has a chelating residue and includes at least one metal ion selected from the group consisting of $Co^{2+}$, $Ni^{2+}$ and $Zn^{2+}$, wherein said metal ion is chelated to the chelating residue.

9. The method according to claim 8, wherein said vinyl polymer containing a hydroxy group is hydrophilic and globular in form.

10. The method according to anyone of claims 6 to 8, wherein said chelating residue is a biscarboxymethylimino group.

11. The method according to claim 1, wherein said metal ion is $Co^{2+}$.

12. The method according to claim 1, wherein said metal ion is $Ni^{2+}$.

13. The method according to claim 1, wherein said metal ion is $Zn^{2+}$.

14. The method according to claim 1, wherein said eluant contacted with the immobilized blue dextran is ethyleneglycol.

15. The method according to claim 1, wherein said eluant contacted with the carrier is an acid solution.

16. The method according to claim 1, wherein said eluant contacted with the carrier is a solution of chelating reagent.

17. The method according to claim 16, wherein said solution of chelating agent is a histidine solution.

18. The method according to claim 16, wherein said solution of chelating reagent is an EDTA solution.

19. The method according to claim 1, wherein said human $\beta$-interferon is produced by a human fibroblast.

20. The method according to claim 1, wherein said human interferon is produced by a microorganism to which interferon genes are integrated.

21. The method according to claim 1, wherein said immobilized blue carrier is a carrier including a coupling of the CI reactive blue 2 to the cross-linked agarose gel via an ether linkage and said carrier is water-insoluble polysaccharide derivative having a chelating residue and including at least one metal ion selected from the group consisting of $Co^{2+}$, $Ni^{2+}$ and $Zn^{2+}$, wherein said metal ion is chelated to the chelating residue.

22. The method according to claim 21, wherein said metal ion is $Zn^{2+}$.

* * * * *